United States Patent [19]

Uzan

[11] Patent Number: 5,849,721
[45] Date of Patent: Dec. 15, 1998

[54] SULFATED POLYSACCHARIDES OBTAINED FROM HEPARIN, PREPARATION PROCESS, PHARMACEUTICAL COMPOSITION AND USE THEREOF

[75] Inventor: André Uzan, Paris, France

[73] Assignee: Rhone-Poulenc Rorer S.A., Antony Cedex, France

[21] Appl. No.: 467,657

[22] Filed: Jun. 6, 1995

Related U.S. Application Data

[63] Continuation of Ser. No. 284,518, filed as PCT/FR93/00114 Feb. 4, 1993, abandoned.

[30] Foreign Application Priority Data

Feb. 7, 1992 [FR] France .................................. 92 01383

[51] Int. Cl.$^6$ .......................... A61K 31/725; C08B 37/10
[52] U.S. Cl. ............................ 514/56; 514/822; 514/824; 536/21
[58] Field of Search ............................ 514/56, 822, 824; 536/21

[56] References Cited

U.S. PATENT DOCUMENTS 4,818,816 4/1989 Petitou et al. .......................... 536/55.2
5,389,618 2/1995 Debrie ...................................... 514/56

FOREIGN PATENT DOCUMENTS

90/04607 5/1990 WIPO .
91/15217 10/1991 WIPO .

OTHER PUBLICATIONS

Mestre et al. *Thromb. Res.* 1985, 38, 389–399.

Kovensky et al. *Thromb. Haemostas.* 1990, 63(3), 488–492.

*Primary Examiner*—Kathleen K. Fonda
*Attorney, Agent, or Firm*—Raymond S. Parker, III

[57] ABSTRACT

This invention relates to mixtures of sulfated oligosaccharides which possess antithrombotic properties and are useful for the treatment and prevention of venous and arterial thrombosis, prevention of arterial thrombotic accidents, and in the prevention of thrombosis in surgical equipment, to pharmaceutical compositions including such mixtures, to processes for preparing such mixtures, and to the use of such mixtures in the prevention of thrombosis in surgical equipment.

14 Claims, 5 Drawing Sheets

SULFATED POLYSACCHARIDES OBTAINED FROM HEPARIN, PREPARATION PROCESS, PHARMACEUTICAL COMPOSITION AND USE THEREOF

This is a continuation of application Ser. No. 08/284,518 filed on Aug. 8, 1994, now abandoned, which is the U.S. national stage entry under 35 U.S.C. 371 of PCT/FR93/00114, filed on Feb. 4, 1993.

The present invention relates to the field of low-molecular-weight polysaccharides. More particularly, it relates to oligosaccharide compositions having excellent pharmacological and antithrombotic properties.

Antithrombotic treatments generally make use of two large categories of agents, namely anticoagulants and anti-platelet agents.

Among the anticoagulants, anti-vitamin K compounds constitute a very important family. Since these compounds are active via the oral route, they are used in numerous indications. However, their use is still limited by certain disadvantages, and in particular the risks of haemorrhaging which they cause and the difficulty of adapting the dosage to a long-term treatment.

Heparins constitute the second category of anticoagulants. They are biological substances of extraction from the family of glycosaminoglycans composed of oligosaccharides having variable chain lengths and degrees of sulphation. More precisely, the molecular weights of the chains constituting non-fractionated heparin are generally spread between 2,000 and 40,000 daltons. Heparins are used in different types of thrombosis, in particular in the treatment or prevention of venous thrombosis, possibly in combination with other therapies.

The disadvantage of heparins resides in their high anticoagulant activity, which may bring about haemorrhaging, and in their sensitivity to certain inhibitory factors of blood such as platelet factor 4, which necessitates the use of relatively large doses.

Moreover, heparins are very heterogeneous products. It is thus difficult to evaluate their mechanism of action, to assess the contribution of each of the components in the overall activity of heparin and, consequently, to increase the antithrombotic activity without increasing the side effects. Developments in scientific knowledge in this field have revealed that the biological properties, that is to say the effects on blood coagulation, as well as the pharmacological properties, that is to say the in vivo antithrombotic activities, of these oligosaccharides vary according to their molecular weight.

A first solution to the abovementioned disadvantages has been provided by low-molecular-weight heparins. These heparins are mixtures of sulphated oligosaccharides whose molecular weights are generally spread between 2,000 and 10,000 daltons. These heparins are obtained by fractionation of the oligosaccharide chains of heparin (for example by gel permeation according to Barrowcliffe et al., Thrombosis research 12 (1977) 27–36), or by fragmentation (depolymerization) of the oligosaccharide chains of heparin using chemical or enzymatic agents. In particular, the depolymerization has been described by treatment of a heparin ester in the presence of a strong base (EP 40144). It may also be performed by treatment of heparin in the presence of nitrous acid, or by the action of a heparinase (EP 64452). These various processes lead to mixtures of oligosaccharides having the general structure of the polysaccharides constituting heparin, but having a lower weight-average molecular weight. These modifications are generally reflected in a better bioavailability and a minimal effect on bleeding relative to non-fractionated heparin.

More particularly, research efforts have essentially been oriented towards mixtures derived from heparin having very short oligosaccharide chains. Thus, Patent EP 27089 indicates that mixtures of oligosaccharides derived from heparin not containing more than 8 saccharide units have a specific antithrombotic activity which is superior to heparin. In the same way, hexasaccharides have been prepared and their antithrombotic properties studied (EP 64452). There may also be mentioned the more recent Patents EP 84 999 and EP 301 618 on polysaccharides such as hexa-, penta- and tetrasaccharides derived from heparin.

However, the products hitherto described have not made it possible to resolve the problems encountered with heparins in a totally satisfactory manner. In particular, most of the low-molecular-weight heparins have an inhibitory action towards thrombin (anti-IIa activity) which is more than 6 times lower than that of heparin. Experimentally on a standard thrombosis model such as that of Wessler in rabbits, the antithrombotic doses are very much greater than those of heparin.

The Applicant has now shown that it is possible to obtain, from native or depolymerized heparins, mixtures of oligosaccharides which have excellent biological and pharmacological properties and, consequently, better therapeutic potential.

Indeed, the Applicant has unexpectedly found that when a mixture of oligosaccharides is prepared for which the molecular distribution is characterized by a proportion equal to or greater than 70% of sulphated oligosaccharides of molecular weight between 5,400 and 7,800 daltons and at least 5% of sulphated oligosaccharides of molecular weight greater than 6,900 daltons, having an anti-IIa activity greater than approximately 60 IU/mg and preferably equal to or greater than approximately 70 IU/mg, this preparation retains the advantages of good bioavailability and of negligible effects on bleeding of the low-molecular-weight heparins, but has the additional advantage of an increased inhibitory power towards thrombin, and a superior antithrombotic activity with an at least equal duration of action.

One subject of the invention thus resides in a mixture of sulphated oligosaccharides having the general structure of the oligosaccharides constituting heparin, characterized in that it comprises at least 70% of oligosaccharides having a molecular weight between 5,400 and 7,800 daltons, at least 5% of oligosaccharides having a molecular weight greater than 6,900 daltons, and in that it has an anti-IIa activity greater than approximately 60 IU/mg and preferably equal to or greater than approximately 70 IU/mg.

Such a mixture unites for the first time the advantages of non-fractionated heparin and those of low-molecular-weight heparins.

Compared with native heparin, the mixtures of the invention additionally have a less pronounced activity to the inhibitory factors of blood such as platelet factor 4, which increases their therapeutic potential.

Other advantages of the mixtures of the invention reside in particular in the reduction of certain undesirable side effects, such as the thrombocytopenic effect. One of the disadvantages of the known mixtures derived from heparin originates from the fall which they may cause in the number of platelets. This undesirable effect is strongly decreased when the mixtures of the invention are employed.

The abovementioned properties make possible a particularly effective pharmacological use, especially in the prophylaxis and treatment of venous or arterial thrombosis. In addition, they should make it possible to use larger doses in vivo without increasing the risks of haemorrhaging.

The mixtures of the invention more preferably comprise at least 10% of oligosaccharides having a molecular weight greater than 6,900 daltons.

Moreover, preferred mixtures of the invention comprise 70% of oligosaccharides having a molecular weight between 5,700 and 7,500 daltons.

Even more preferably, the mixtures of the invention comprise at least 60% of oligosaccharides having a molecular weight between 5,700 and 6,900 daltons.

Moreover, the anti-IIa activity of the mixtures of the invention is preferably lower than their anti-Xa activity.

In a preferred mode, the mixtures of the invention are more particularly fractions of depolymerized heparin. As indicated above, depolymerized heparin may be obtained by any chemical, enzymatic or other technique, known to a person skilled in the art, which makes it possible to fragment the oligosaccharide chains of heparin. In particular, the processes described in Patents EP 40144, EP 64452, EP 37319 or EP 337327 are suitable for the invention.

Even more preferably, the mixtures of the invention consist of oligosaccharides having a 2-O-sulpho-4-enopyranosuronic acid at one of their ends.

A particularly advantageous mixture consists of a heparin fraction depolymerized by the action of a base on a heparin ester.

Another subject of the invention relates to a process for the preparation of a mixture as defined above, characterized in that a heparin or a depolymerized heparin is fractionated by gel filtration.

The process of the invention involves several parameters, the control of which makes it possible to calibrate the molecular weight and molecular distribution of the final mixture. In particular, these parameters are the ionic strength of the eluent and the nature of the support used.

More preferably, the fractionation is characterized in that the steps consisting in (i) dissolving the starting heparin or depolymerized heparin in the eluent, (ii) passing the solution thus obtained through a column containing at least the solid support for the gel filtration, which has been equilibrated beforehand with the same eluent, and (iii) recovering the fractions of desired molecular weight, are successively performed.

In a particular embodiment of the invention, a depolymerized heparin is used as starting heparin Such a heparin may be obtained according to the processes described in Patents EP 40144, EP 64452, EP 37319 or EP 337327.

Even more preferably, a heparin is used which has been depolymerized by the action of a base on a heparin ester, such as for example according to the technique described in Patent EP 40 144. In particular, the depolymerization may be performed in an aqueous medium or in an inert organic solvent, under the action of an organic or inorganic base such as for example sodium hydroxide or potassium hydroxides an alkali metal carbonate or a tertiary amine (triethylamine, triethylenediamine, etc.). The action of the base on the ester makes it possible to perform a partial and controlled depolymerization of heparin without altering its general structure.

As eluent which may be used in the process of the intention, there may be mentioned various types of saline solutions, such as sodium chloride solutions, However, the Applicant has shown that, in order to obtain fractions having the best properties, it is particularly advantageous to perform the fractionation using an eluent chosen from phosphate buffers, in particular such as potassium phosphate, sodium phosphate or $NH_4H_2PO_4$. It is also possible to use solutions of $NaClO_4$ or $NH_4NO_3$, which allow mixtures having excellent characteristics to be obtained.

The concentration of the eluent, and thus its ionic strength, are adapted to the desired final mixture. In particular, the concentration of the eluent is advantageously less than 1M and even more preferably between 0.1 and 0.5M.

When a phosphate buffer is used, it is particularly advantageous to work at concentrations close to 0.2M In the second step of the process of the invention, the support used is generally chosen according to the average molecular weight of the starting product (native, depolymerized etc. heparin), the final product desired, and the behaviour of the starting mixture in the eluent used A gel of polyacrylamide-agarose type is advantageously used as support. By way of example, there may be mentioned the gels AcA 54, AcA 202, sephadex G25 or G50, or alternatively Biogel P30, which give good results.

In a first particularly advantageous embodiment of the process of the invention, during the second step of the fractionation, the solid support is distributed in several columns arranged in series. This variant of the invention makes it possible to employ large final amounts of support for the gel filtration, without the disadvantages of the prior art, namely, essentially, the packing phenomena. In this way, the separation is much cleaner, including the high molecular weight range, in a single fractionation operation, and the supports may more readily be regenerated.

The number of columns used is adapted by a person skilled in the art, depending on the volume and nature of the gel employed, so as to obtain the best balance between the efficiency of the separation and the harmful effect due to the packing of the gel.

For practical implementation reasons, it is generally preferred to use a number of columns less than 20 in the second step of the process.

As a guide, 40 liters of AcA 202 gel may be distributed between 10 columns of 4 liters, or 130 liters between 10 columns of 13 liters.

In another particularly advantageous embodiment of the process of the invention, at least 2 types of support are used successively during the second step of the fractionation, which supports have different separation characteristics. This variant of the invention allows a better quality of final fractionation to be obtained.

By way of example, the fractionation may be performed on the following sequence of gels:

AcA 202- AcA 54- AcA202.

For a better implementation of the invention, it is important to employ large amounts of gel, in order to achieve a cleaner separation and to obtain greater homogeneity. Taking into account, however, the fairly slow flow rates used for this type of gel filtration, the volume of gel should be adapted to the amount of product to be separated, in order to obtain the best balance between the separation and the longitudinal diffusion effect.

In the process of the invention, the starting heparin (g)/volume of gel (1) ratio is advantageously less than 2 and even more preferably between 0.5 and 1.5.

Another aim of the invention relates to a pharmaceutical composition having a mixture as defined above as active principle. Such a composition may be used particularly advantageously in the prophylaxis or the treatment or the prevention of thrombotic accidents. More precisely, it may be used:

in the prevention of venous thrombosis in risk situations, in the prevention of arterial thrombotic accidents, in particular in the case of myocardial infarction, in post-operative care, in the prevention of venous thrombosis in surgical patients, or alternatively in the prevention of thrombosis in the surgical equipment.

The present invention will be described more fully with the aid of the examples which follow, which should be considered as a guide and non-limiting. In these examples, the physicochemical, biological and pharmacological characteristics of the mixtures were determined according to the following techniques:

Molecular weight and molecular distribution

The molecular weights and the molecular distributions of the products are determined by high pressure liquid chromatography with two columns in series, for example those marketed under the name TSK G3000 XL and TSK G2000 XL coupled with a refractometric detector.

The eluent used is 0.5M lithium nitrate and the flow rate is 0.6 ml/minute. The system is calibrated with monodisperse standards obtained by fractionation of enoxaparine (Pharmuka) by exclusion chromatography on agarose-polyacrylamide (IBF) according to the technique described by Barrowcliffe et al., Thromb. Res., 12, 27–36 (1977–78) or D. A. Lane et al., Thromb. Res. 12, 257–271 (1977–78). The results are calculated using the GPC6 program (Perkin Elmer).

Anti-Xa activity

The technique used is that described by Teien A. N. and Lie M. in Thrombosis research 10 (1977) 399–410, with as standard the first international standard for low-molecular-weight heparins (WHO LMWH1).

Anti-IIa activity

The technique used is that described by Anderson L. O. et al., in Thrombosis research 15 (1979) 531–541, with as standard the first international standard for low-molecular-weight heparins (WHO LMWH1).

APTT

The technique used is the "Actimat" technique (Bio Mérieux) as described by Bell W. N. and Alton H. G. in Nature 174 (1954) 880–881.

Venous thrombosis in rabbits

The technique used is that described by Wessler S. in Journal of Clinical investigation 34 (1955) 647–651.

Bleeding time in rats

The technique used is that described by Palm M. et al., in Thrombosis and haemostasis 64(1) (1990) 127–132.

BRIEF DESCRIPTION OF THE FIGURES

FIG. 2 (A and B): kinetics of the anti-Xa activity of the mixtures of the invention in rabbits: comparison with another low-molecular-weight heparin.

FIG. 3 (A and B): kinetics of the anti-IIa activity of the mixtures of the invention in rabbits: comparison with another low-molecular-weight heparin.

EXAMPLE 1

Preparation of a depolymerized heparin

To a solution of 10 g of sodium heparinate in 100 ml of water is added a solution of 25 g of benzethonium chloride in 125 ml of water. The product obtained at room temperature is filtered, washed with water and then dried. 15 g of benzethonium heparinate thus obtained are dissolved in 75 ml of methylene chloride, to which are added 15 ml of benzyl chloride. The solution is heated at a temperature between 25° and 35° C. for 25 hours. 90 ml of 10% sodium acetate solution in methanol are then added, followed by filtration, washing with methanol and drying. 10 g of heparin benzyl ester obtained under the conditions described above, in the sodium salt form, are dissolved in 250 ml of water. To this solution, heated to approximately 60° C., is added 0.9 g of sodium hydroxide. The temperature is maintained for 1 h 30 at approximately 60° C., and the reaction mixture is subsequently cooled to about 20° C. and neutralized by addition of dilute hydrochloric acid. The concentration of the medium is then adjusted to a 10% content of sodium chloride, and the product is precipitated in 750 ml of methanol, filtered off and dried.

EXAMPLE 2

Preparation of the mixture M1

10 glass columns 100 mm in diameter and 50 cm in height, each containing 4 liters of AcA 202 gel (gel in the form of polyacrylamide-agarose beads, of diameter between 60 and 140 $\mu$m), are used in series for the fractionation:

A solution containing 30 g of heparin which has been depolymerized under the conditions described in Example 1 is placed at the head of the first column and eluted with a mobile phase consisting of 0.2M $KH_2PO_4$ solution, at a flow rate of 300 ml/hour. The fractions are collected at the end of the tenth column.

This treatment allows the oligosaccharide chains to be separated efficiently according to their molecular weight, and to combine them subsequently in order to obtain mixtures having the desired characteristics. The mixture M1 was thus obtained, for which the in vitro biological and physicochemical characteristics are given in Table 1.

EXAMPLE 3

Preparation of the mixture M2

The mixture M2 was obtained by following the same fractionation procedure as that described in Example 2, using 50 g of depolymerized heparin.

The in vitro physicochemical and biological characteristics of the mixture M2 are given in Table 1.

EXAMPLE 4

Preparation of the mixture M5 and of the mixture M6

The mixture M5 was obtained by following the same fractionation procedure as that described in Example 2, from 30 g of depolymerized heparin, but using 10 columns 9 cm in diameter and 50 cm in height.

The mixture M6 was obtained by a first fractionation performed according to the procedure of Example 2, from 150 g of depolymerized heparin on 10 columns 18 cm in diameter and 50 cm in height, with a flow rate of the mobile phase of 1.1 1/hour. The fractions of interest were pooled and the oligosaccharides precipitated by addition of methanol. The recovered solid was subsequently dissolved and then refractionated on the same chromatographic system. The fractions were recovered at the end of the tenth column.

The in vitro biological and physicochemical characteristics of the mixtures M5 and M6 are given in Table 1.

EXAMPLE 5

Comparative Example: Preparation of the mixture M3 and of the mixture M4

The mixture M3 was obtained by following the same fractionation procedure as that described in Example 2. For the mixture M4, after fractionation according to the procedure of Example 2, it was obtained by mixing a fraction coming off at 5,530 daltons (63%) and a fraction coming off at 7,770 daltons (37%).

The in vitro biological and physicochemical characteristics of the mixtures M3 and M4 are given in Table 1.

Figure 1:
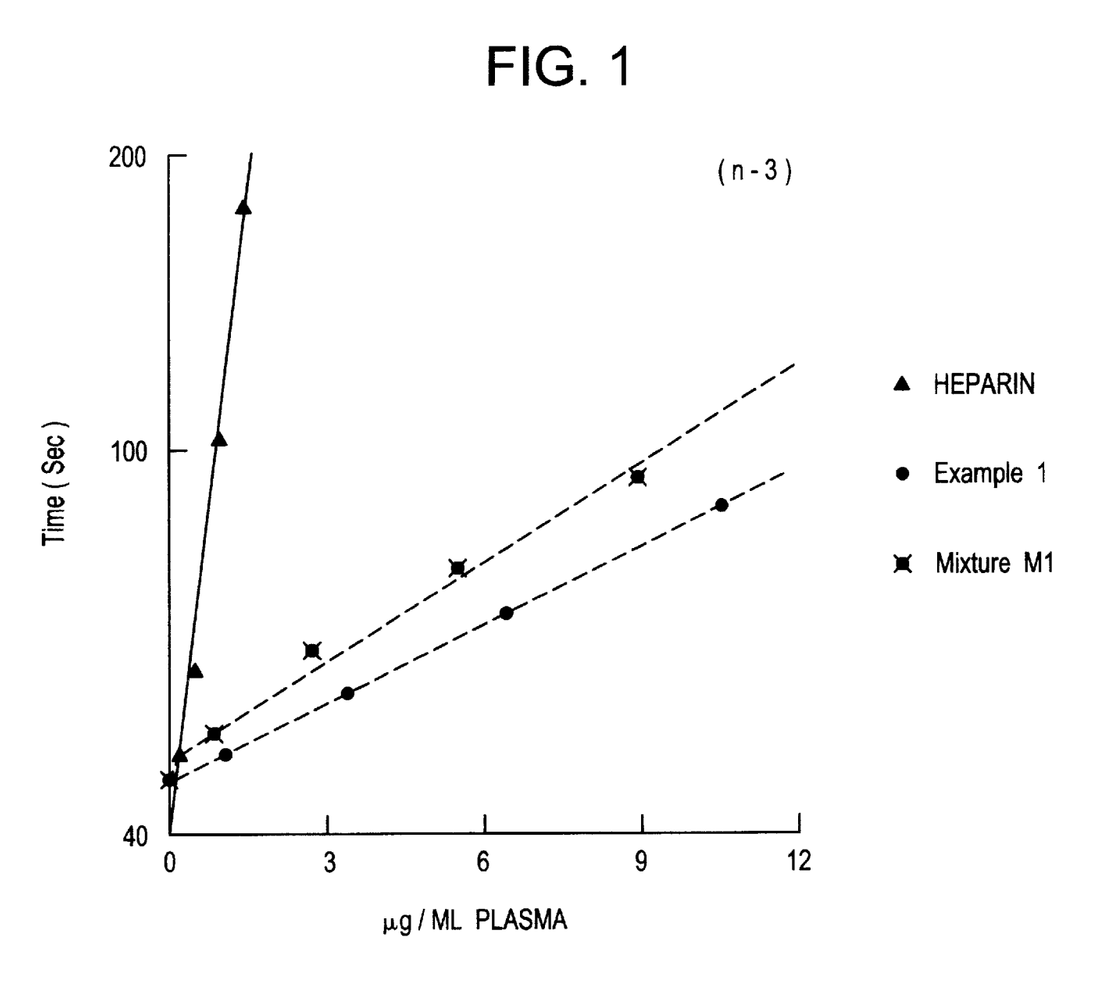
FIG. 1: in vitro APTT activity on human plasma of the mixtures of the invention compared with other heparins.

EXAMPLE 6 in vitro study of the APTT activity on human plasma of the mixtures of the invention The results obtained are presented in FIG. 1. They show clearly that the mixtures of the invention (mixture M1) cause the APTT, on human plasma, to vary much more markedly in vitro than with non-fractionated heparin.

TABLE 1

| Product | M1 | M2 | Ex. 1 | M3 | M4 | M5 | M6 |
|---|---|---|---|---|---|---|---|
| Average molecular weight | 6410 | 6340 | 4280 | 5550 | 6360 | 6420 | 6780 |
| Molecular distribution (% MW) | | | | | | | |
| - > 7,500 | 1 | 5.5 | 9 | 0 | 22 | 3.5 | 3.5 |
| - 7,200 ± 300 | 12.5 | 15 | 3.5 | 0 | 10.5 | 16.75 | 35.25 |
| - 6,600 ± 300 | 47 | 30.5 | 5 | 9 | 10 | 37.5 | 50.75 |
| - 6,000 ± 300 | 35 | 32.5 | 6.5 | 30 | 19.5 | 31.75 | 9.5 |
| - 5,400 ± 300 | 4.5 | 13.5 | 7.5 | 40.5 | 25 | 9.5 | 1 |
| - < 5,100 | 0 | 3 | 68.5 | 20.5 | 13 | 1 | 0.1 |
| In vitro activity | | | | | | | |
| - anti-Xa | 109 | 127 | 94.25 | 116.6 | 130 | 126 | 106 |
| - anti-IIa | 75 | 80 | 27.75 | 41.8 | 78 | 68 | 70 |

EXAMPLE 7

Kinetic study of the anti-Xa and anti-IIa activities in rabbits

This study was performed according to the following procedure:

rabbits: New Zealand (3.5 kg)

volume injected: subcutaneous route: 0.5 ml/kg (abdominal region)

blood samples: 3 ml of blood are withdrawn on 3.1% sodium citrate solution (1/10) from the median artery of the ear at times 0 min, 45 min, 90 min, 3 h, 4 h, 6 h, 8 h.

Figure 2A:
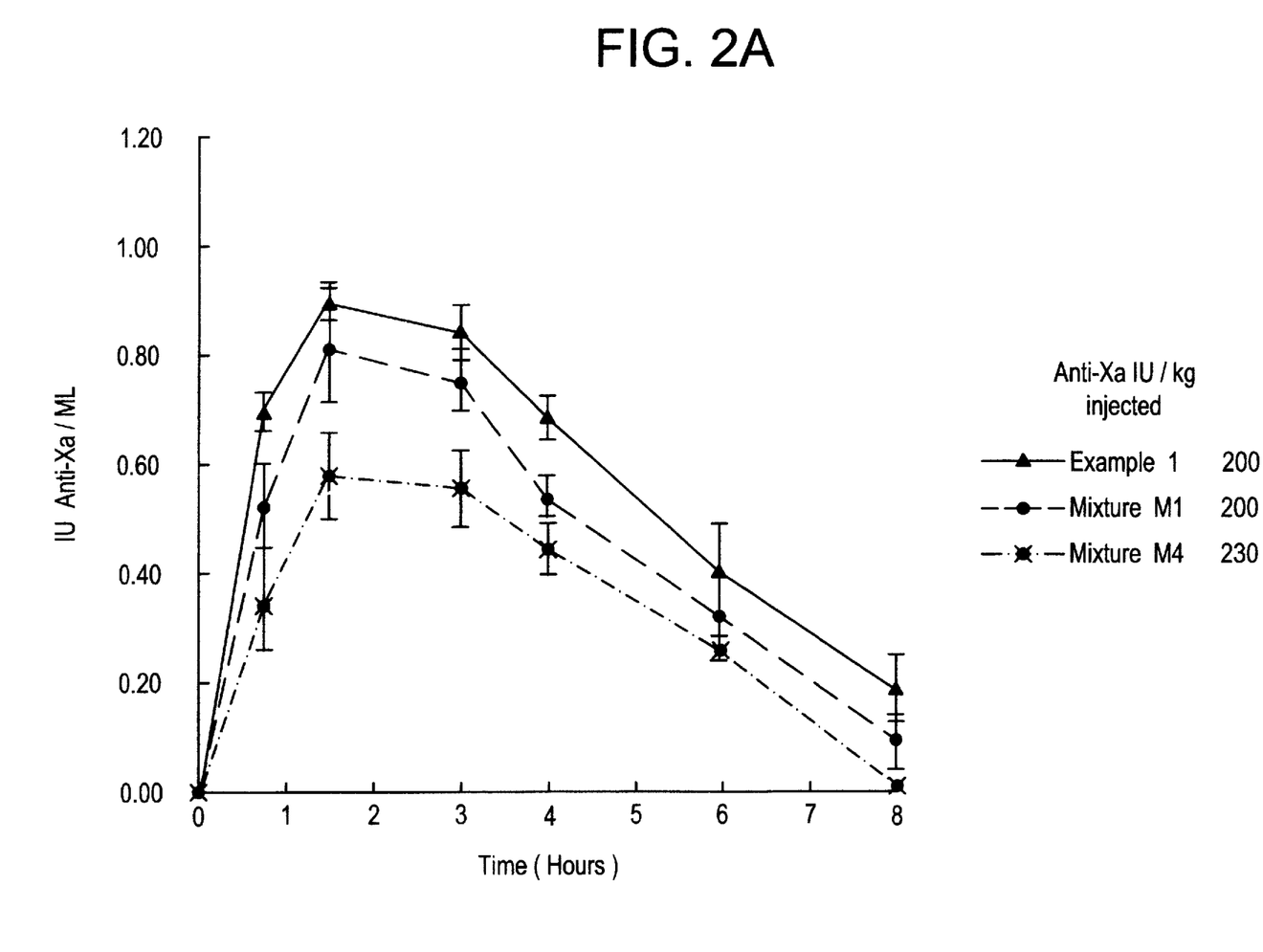
Figure 2B:
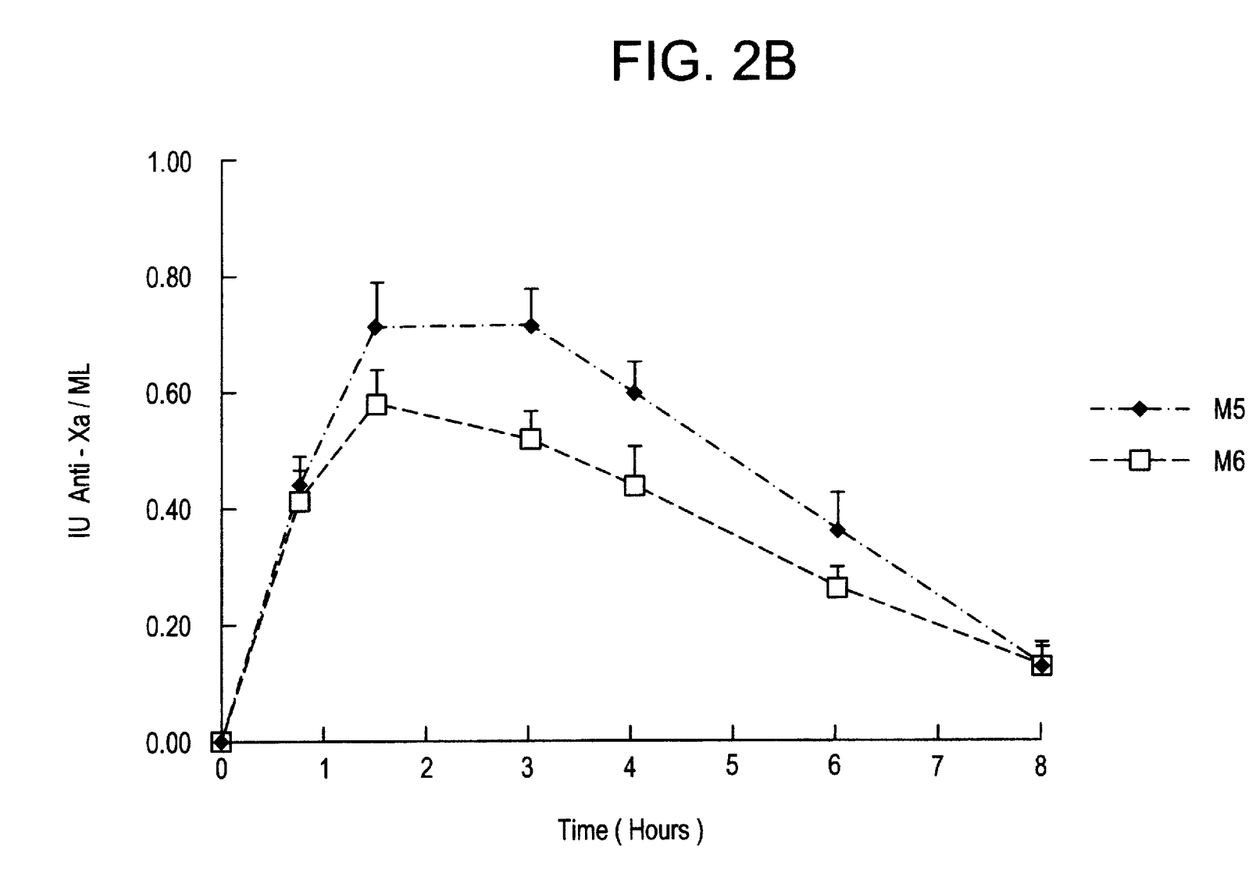
Figure 3A:
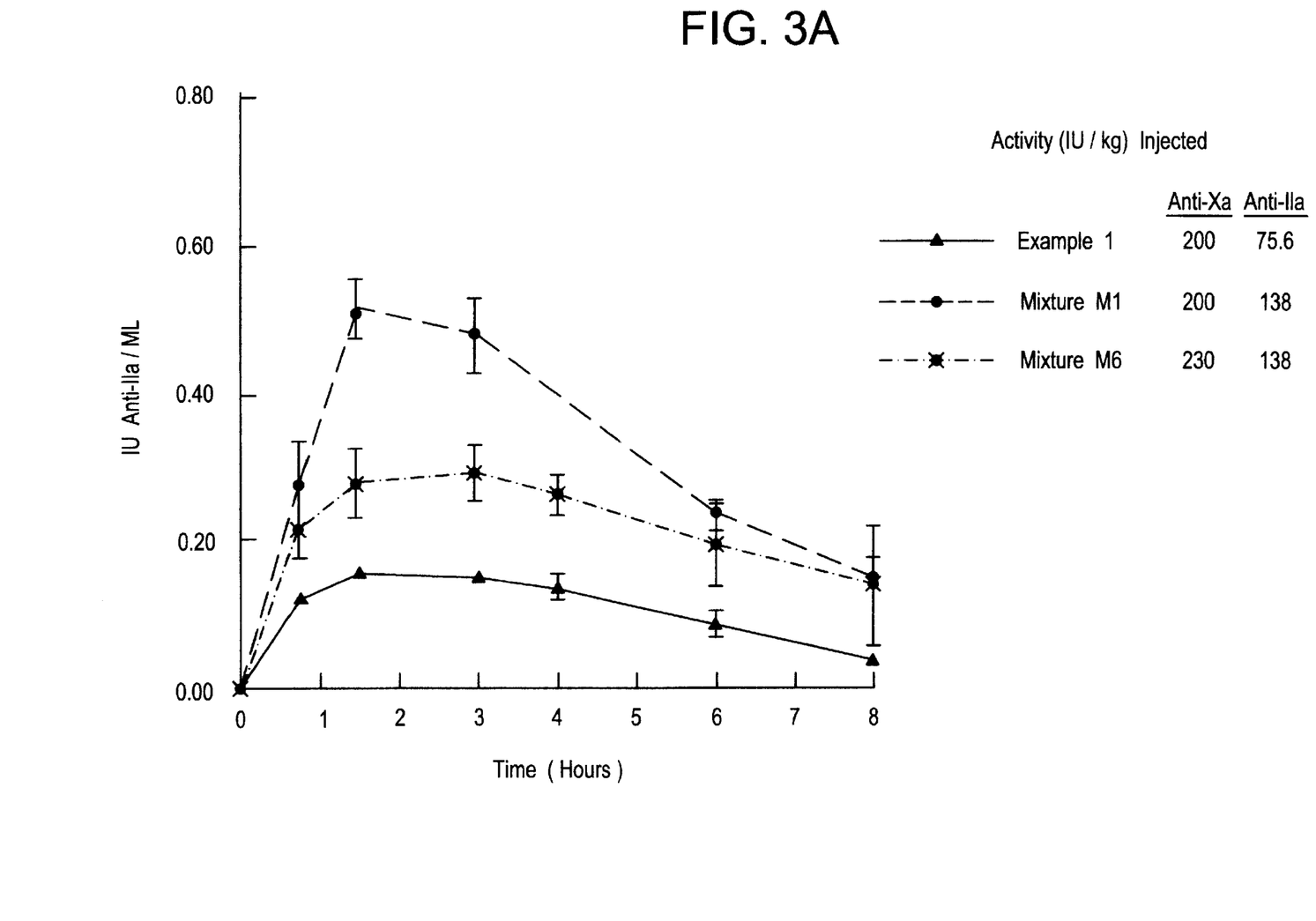
Figure 3B:
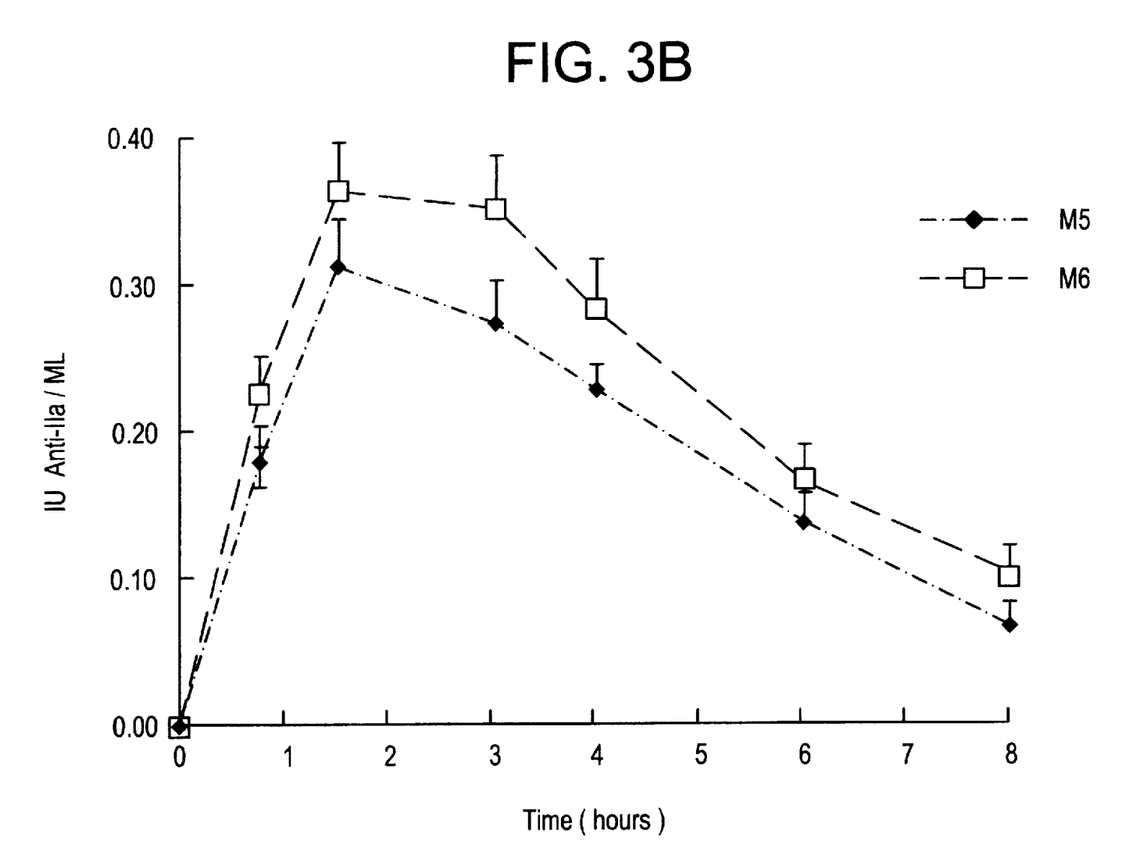

After subcutaneously injecting the rabbit with the mixtures M1, M5 and M6 according to the invention, or with depolymerized heparin according to Example 1, at equal anti-Xa doses, anti-Xa and anti-IIa activities are obtained in the plasma which are:

parallel and comparable for anti-Xa (FIG. 2)

much superior with the mixture of the invention for the anti-IIa activity (FIG. 3).

The same comparison, made with respect to the mixture M4 described in Example 5, shows that the anti-Xa activities of the plasma remain parallel but that there is a very large difference for the anti-IIa activity (FIGS. 2 and 3).

Therefore, these results surprisingly show that the mixtures of the invention have persistent, sustained and high in vivo anti-Xa and anti-IIa activities. These mixtures are accordingly particularly advantageous with respect to non-fractionated heparin, whose in vivo anti-Xa and anti-IIa activities are very short-lived, but also with respect to the low-molecular-weight heparins described in the prior art, whose in vivo anti-IIa activity is very short-lived.

EXAMPLE 8

Study of the in vivo activity of the mixtures of the invention on venous thrombosis in rabbits after intravenous injection.

The results obtained are collated in Table 2. This table shows that the mixture M3 (Example 4), whose molecular distribution is different from that claimed, and depolymerized heparin (Example 1) are less active than the mixture M1 of the invention. In particular, the latter gives an anti-IIa activity which is clearly superior.

EXAMPLE 9

Study of the in vivo activity of the mixtures of the invention on venous thrombosis in rabbits after subcutaneous injection.

The results obtained are collated in Tables 3 and 4. These tables show that the mixtures M1, M5 and M6 are more active than a depolymerized heparin of the prior art (Example 1), and that they have an at least equivalent duration of action.

EXAMPLE 10

Study of the in vivo activity on the bleeding time in rats.

The results presented in the following Table 5 show clearly that the mixtures of the invention (illustrated by the mixtures M1, M5 and M6) cause less bleeding than the other low-molecular-weight heparins. The results given correspond with the increase in the bleeding time in minutes with respect to control values. By way of comparison, at 2 mg/kg, heparin induces an increase in the bleeding time of 13 [lacuna].

TABLE 5

| Dose/Product | M1 | M5 | M6 | Ex. 1 | M4 |
|---|---|---|---|---|---|
| 4 mg/kg | 1.07 ± 0.4 | | | 4 ± 1.1 | 8.6 ± 3.6 |
| 8 mg/kg | 3.0 ± 0.7 | 4.0 ± 0.5 | 9.6 ± 1.8 | 7.9 ± 2.1 | 33.7 ± 8 |

TABLE 2

| | EXAMPLE 1 Anti-Xa = 94.25 IU/mg Anti-IIa = 27.75 IU/mg | | | MIXTURE M1 109 IU/mg 75 IU/mg | | MIXTURE M3 Anti-Xa = 116.6 u/mg Anti-IIa = 41.8 u/mg | | | Control |
|---|---|---|---|---|---|---|---|---|---|
| μg/kg | 318.00 | 265.00 | 212.00 | 183.50 | 257.3 | 214.4 | 171.5 | 107 | 0 |
| Doses anti-Xa | 30.00 | 25.00 | 20.00 | 20.00 | 30 | 25 | 20 | 12.5 | 0 |
| | 8.80 | 7.30 | 5.90 | 13.80 | 10.75 | 8.96 | 7.1 | 4.5 | 0 |

TABLE 2-continued

| | EXAMPLE 1<br>Anti-Xa = 94.25 IU/mg<br>Anti-IIa = 27.75 IU/mg | | MIXTURE<br>M1<br>109 IU/mg<br>75 IU/mg | | MIXTURE M3<br>Anti-Xa = 116.6 u/mg<br>Anti-IIa = 41.8 u/mg | | | Control | |
|---|---|---|---|---|---|---|---|---|---|
| μ/kg anti-IIa μ/kg | | | | | | | | | |
| n | 5 | 5 | 8 | 8 | 5 | 8 | 8 | 5 | 8 |
| Weight of the thrombus | 2.24 ± 2.24 | 12.4 ± 8.4 | 53.2 ± 25 | 6.44 ± 3.44 | 27.74 ± 17.96 | 27.5 ± 12.66 | 50.5 ± 15 | 75.3 ± 25 | 120.7 ± 34.1 |
| Number of rabbits without thrombus | 4/5 | 2/5 | 3/8 | 5/8 | 2/5 | 2/8 | 1/8 | 0/5 | 0/8 |
| Anti-Xa plasma μ/ml | 0.370 ± 0.026 | 0.356 ± 0.039 | 0.193 ± 0.015 | 0.268 ± 0.02 | 0.363 ± 0.023 | 0.296 ± 0.008 | 0.241 ± 0.022 | 0.125 ± 0.011 (n = 4) | |
| Anti-IIa plasma μ/ml | 0.100 ± 0.004 | 0.069 ± 0.011 | 0.062 ± 0.004 | 0.196 ± 0.009 | 0.100 ± 0.008 | 0.130 ± 0.006 | 0.093 ± 0.008 | 0.054 ± 0.005 (n = 4) | |

TABLE 3

| | Control | EXAMPLE 1<br>Anti-Xa = 94.25 IU/mg<br>Anti-IIa = 27.75 IU/mg | | | MIXTURE M1<br>109 IU/mg<br>75 IU/mg | | |
|---|---|---|---|---|---|---|---|
| Time | | 90 minutes | 240 minutes | 360 minutes | 90 minutes | 240 minutes | 360 minutes |
| anti-Xa IU/kg | | 300.00 | 300.00 | 300.00 | 200.00 | 200.00 | 200.00 |
| Doses anti-IIa IU/kg | | 88.33 | 88.33 | 88.33 | 137.98 | 137.98 | 137.98 |
| mg/kg | | 3.18 | 3.18 | 3.18 | 1.83 | 1.83 | 1.83 |
| n | 8 | 5 | 5 | 5 | 5 | 5 | 5 |
| Weight of the thrombus | 73.10 | 0.00 | 0.00 | 91.00 | 0.00 | 0.00 | 111.50 |
| | 62.70 | 13.60 | 47.20 | 19.50 | 44.80 | 19.00 | 12.20 |
| | 41.00 | 4.10 | 0.00 | 2.90 | 18.50 | 0.00 | 60.40 |
| | 68.00 | 0.00 | 22.00 | 0.00 | 3.20 | 23.40 | 7.10 |
| | 114.00 | 10.40 | 3.60 | 15.20 | 0.00 | 0.00 | 0.00 |
| | 100.60 | | | | | | |
| | 339.70 | | | | | | |
| | 166.90 | | | | | | |
| Mean ± SEM | 120 ± 34 | 5.62 ± 2.75 | 14.56 ± 9.12 | 25.72 ± 16.72 | 13.30 ± 8.60 | 8.48 ± 5.24 | 38.24 ± 21.20 |
| Student test | | p < 0.05 | p < 0.05 | NS | p < 0.05 | p < 0.05 | NS |
| Number of rabbits without thrombus | 0/8 | 2/5 | 2/5 | 1/5 | 2/5 | 3/5 | 1/5 |
| Anti-Xa plasma μ/ml | | 0.89 ± 0.10 | 0.89 ± 0.125 | 0.47 ± 0.005 | 0.61 ± 0.06 | 0.61 ± 0.06 | 0.40 ± 0.04 (N = 4) |
| Anti-IIa plasma μ/ml | | 0.16 ± 0.02 | 0.16 ± 0.023 | 0.12 ± 0.013 | 0.55 ± 0.04 | 0.55 ± 0.04 | 0.32 ± 0.02 (n = 4) |

TABLE 4

| | CONTROL | MIXTURE M5 | | MIXTURE M6 | |
|---|---|---|---|---|---|
| Time | | 90 minutes | 90 minutes | 90 minutes | 90 minutes |
| Anti-Xa doses IU/kg | | 200.00 | 300.00 | 200.00 | 300.00 |
| n | 6 | 8 | 5 | 8 | 2 |
| Weight of the thrombus | 126.9 | 28.4 | | 31.1 | 0 |
| | 77.2 | 77.3 | 0 | 135 | 0 |
| | 110.2 | 25.9 | 44.5 | 24.6 | |
| | 150.7 | 0 | 0 | 0 | |
| | 180.8 | 0 | 0 | 0 | |
| | 223.0 | 0 | 0 | 102 | |
| | | 83.9 | | 0 | |
| | | 0 | | 23.2 | |
| Mean ± SEM | 144.8 ± 21 | 26.93 ± 14.38 | 8.9 ± 8.9 | 39.48 ± 18.06 | 0 |
| Number of rabbits without thrombus | 0/6 | 4/8 | 4/5 | 3/8 | 0/2 |

I claim:

1. A mixture of sulphated oligosaccharides obtained from native or depolymerized heparin comprising at least 70% of oligosaccharides having a molecular weight between 5,400 and 7,800 daltons, at least 5% of oligosaccharides having a molecular weight greater that 6,900 daltons, and having an anti-IIa activity greater than approximately 60 IU/mg.

2. The mixture according to claim 1 comprising at least

70% of oligosaccharides having a molecular weight between 5,700 and 7,500 daltons.

3. The mixture according to claim 2 comprising at least 60% of oligosaccharides having a molecular weight between 5,700 and 6,900 daltons.

4. The mixture according to claim 1 comprising at least 10% of oligosaccharides having a molecular weight greater than 6,900 daltons.

5. The mixture according to claim 1 having an anti-IIa activity equal to or greater than 70 IU/mg.

6. The mixture according to claim 1 comprising a fraction of heparin.

7. The mixture according to claim 1 comprising a fraction of depolymerized heparin.

8. The mixture according to claim 7 comprising oligosaccharides having a 2-O-sulpho-4-enopyranosuronic acid at one of their ends.

9. The mixture according to claim 8 comprising a heparin fraction which has been depolymerized by the action of a base on a heparin ester.

10. A method for the prevention of venous and arterial thrombosis comprising administering to a patient in need of such prevention an antithrombotic effective amount of the mixture of sulphated oligosaccharides according to claim 1.

11. A method for the prevention of arterial thrombotic accidents comprising administering to a patient in need of such prevention an antithrombotic effective amount of the mixture of sulphated oligosaccharides according to claim 1.

12. A method for the prevention of arterial thrombotic fortuitous incidents during myocardial infarction comprising administering to a patient in need of such prevention an antithrombotic effective amount of the mixture of sulphated oligosaccharides according to claim 1.

13. A method for the prevention of venous thrombosis during post-operative care comprising administering to a patient in need of such prevention an antithrombotic effective amount of the mixture of sulphated oligosaccharides according to claim 1.

14. A method for prevention of thrombosis in surgical equipment comprising administering, to a patient undergoing a surgical procedure using said surgical equipment, an antithrombotic effective amount of the mixture of sulphated oligosaccharides according to claim 1.

* * * * *